United States Patent [19]

Hoff

[11] Patent Number: 4,801,552
[45] Date of Patent: Jan. 31, 1989

[54] METHOD AND A SPECTROMETER FOR MEASURING ABSORBANCE DIFFERENCE SPECTRA OF RADICAL REACTIONS

[75] Inventor: Arnold J. Hoff, Leiden, Netherlands

[73] Assignee: Ryksuniversiteit Leiden, Leiden, Netherlands

[21] Appl. No.: 919,000

[22] PCT Filed: Feb. 10, 1986

[86] PCT No.: PCT/NL86/00004

§ 371 Date: Sep. 30, 1986

§ 102(e) Date: Sep. 30, 1986

[87] PCT Pub. No.: WO86/04673

PCT Pub. Date: Aug. 14, 1986

[30] Foreign Application Priority Data

Feb. 6, 1985 [NL] Netherlands ............... 8500363

[51] Int. Cl.[4] .................. G01J 3/42; G01N 21/62
[52] U.S. Cl. .................... 436/173; 422/68; 436/149
[58] Field of Search ........... 356/319, 326, 327, 368; 422/68; 436/149, 173

[56] References Cited

U.S. PATENT DOCUMENTS 3,442,592 5/1969 Grosjean ..................... 356/80

OTHER PUBLICATIONS

Hoff et al.; Magneto-Optical Absorbance Difference Spectroscopy; Chem. Phys. Lett. vol. 114, No. 1, 15 Feb. 1985, pp. 39–43.
Ke et al.; Versatile Spectrophotometer for Photosynthesis and Other Biophysical Measurements; Rev. Sci. Instrum. 56(1) Jan. 1985, pp. 26–31.
Den Blanken et al.; High-Resolution Optical Absorption-Difference Spectra of the Triplet State of the Primary Donor in Isolated Reaction Centers of the Photosynthetic Bactria Rhodopseudomonas Sphaeroides R-26 and Rhodopseudomonas Viridis Measured with Optically Detected Magnetic Resonance at 1.2K. Biochim. Biophysica. Acta. 681 (1982) pp. 365–374.
Kolesnikova et al.; Study of Charge Separation at the Centers of Photosystem II of Higher Plants by Magnetic Modulation, Abs. 103807 1982.
Bartiromo et al.; An Apparatus for Magneto-Optical Spectroscopy by Magnetic Modulation, J. of Phys. E. 10, 1977.

*Primary Examiner*—Benoit Castel
*Assistant Examiner*—Lyle Alfandary Alexander
*Attorney, Agent, or Firm*—Parmelee, Bollinger & Bramblett

[57] ABSTRACT

A method and a spectrometer for measuring the absorbance difference spectra of radical reactions using a modulated perturbation of the concentration of reactants in, for example, radical complexes induced by radiation, whereby the yield of substances and/or molecular states produced by recombination and by escaping radicals is influenced. A modulated magnetic field is exerted on the material, and the changes in absorbance of the material generated as a result thereof are phasesensitively detected for a wide frequency range.

The spectrometer is provided with means for radiation of the material to be investigated, means for receiving the same material, cooling and/or heating means, detection means for the detection of the resulting absorbance spectrum of the said material, and further with a device for exerting a modulated magnetic field on the material. The detection means have a phasesensitive detector which converts the change in absorbance generated into a dc absorbance. The cooling and/or heating can be adjusted to a temperature in a wide temperature range.

3 Claims, 4 Drawing Sheets

METHOD AND A SPECTROMETER FOR MEASURING ABSORBANCE DIFFERENCE SPECTRA OF RADICAL REACTIONS

The invention relates to a method for measuring absorbance difference spectra of radical reactions using a modulated perturbation of the concentration of reactants in, for example, radical complexes induced by radiation, the yield of substances and/or molecular states produced by recombination and by escaping radicals being influenced. The invention also relates to a spectrometer for carrying out the above-named method, which spectrometer is provided with means for radiation of the material to be investigated, means for receiving the said material, cooling and/or heating means, and detection means for the detection of the resulting absorbance spectrum of the said material.

The above method and spectrometer are known from the article by H. J. den Blanken and A. J. Hoff in Biochem. Biophys. Acta 681 (1982), pages 365–374. In this known method the magnetic resonance of intermediate triplet states in photosynthetic material is detected by means of triplet-minus-singlet absorbance difference (T-S) spectra. In this process a modulated perturbation of the concentration of intermediate triplet states is produced by means of irradiated microwaves which resonate between two of the triplet sublevels. The resulting change in the absorbance is then detected and recorded as a function of wavelength. In this manner an absorbance difference spectrum is obtained and recorded which reflects the bleaching of tripletcarrying pigments, and bandshifts and the appearance of new bands due to triplet-induced changes in the electrostatic interaction between pigments which adjoin the pigment carrying the triplet state.

Although good results have been obtained with the above method in the investigation of reactions in photosynthetic pigment materials such as plants, alga or bacteria, this method can be performed only in a limited range of temperature at very low temperatures near the absolute zero point to avoid spin-lattice relaxation between the triplet sublevels. As a result of this, temperature-induced changes in the triplet-minus-singlet absorbance difference spectrum, which reflect changes in pigment configuration or the presence of other excited states such as charge transfer states cannot be detected. In addition, this method is limited only to investigation of reactions in which intermediate triplet states are present.

The object of the invention is to eliminate the above-named problems and to provide a method and a spectrometer with which absorbance difference spectra of radical complexes can be measured over a wide temperature range with great accuracy so that all the substances taking part in a radical reaction can be investigated.

According to the invention this is achieved in a method of the type mentioned in the introduction in the manner that a modulated magnetic field is exerted on the material and in that the changes in the absorbance of the material generated as a result thereof are phase-sensitively detected over a wide frequency range, it being possible to vary the temperature of the material over a large adjustment range which may include room temperature.

According to the invention the spectrometer mentioned in the introduction is further characterized by a device for exerting a modulated magnetic field on the material, the detection means being provided with a phase-sensitive detector which converts the changes in absorbance generated into a dc absorbance, the cooling and/or heating means being adjusted to a temperature in a wide temperature range.

With the method and spectrometer according to the invention radical reactions can be investigated with advantage to determine, for example, the difference in concentration of reactants. The present so-called magneto-optical difference spectroscopy (MODS) measurements can be performed with great accuracy; thus, a signal/noise ratio is obtained which may be 1,000 times better than in the prior art. This method can also be used in any frequency range where absorbance of radiation occurs.

Thus, with the present method absorbance difference spectra have been measured of a photosynthetic bacterium *Rhodopseudomonas viridis* (abbreviated: Rps. viridis). On exposure to radiation a triplet state is formed in the said Rps. viridis on the primary electron donor D by recombination of the photoinduced charges on the primary donor and the primary electron acceptor $A_1$. On applying the present method significant changes in the T-S spectrum appear to occur around 830 nm between 300 and 160K. Elsewhere temperature-dependant changes in this spectral region have already been observed for reaction centres of *Rhodopseudomonas sphaeroides* by means of flash spectroscopy (see V. A. Shuvalov and W. W. Parson, Proc. National Academy of Science USA 78 (1981), pages 957–961). At the time these changes were ascribed to a charge transfer state between the donor D and a neighbouring bacteriochlorophyll (BChl) pigment which possibly functions as a transient acceptor $A_0$. This state was thought to be associated with the triplet state $^3D$ at higher temperatures. The spectra of Rps. viridis obtained by the present method which are accurately resolved against temperature make this interpretation unlikely. These spectral changes are virtually certainly due to a temperature-dependent bandshift of one of the associated bacteriochlorophyll molecules which functions as an early transient acceptor $A_0$.

From the thesis of H. Rademaker of the State University of Leiden (1982) the use of a modulated magnetic field perturbation is known per se, but only for the investigation of the influence on luminescence. In this case only a very limited frequency range was employed.

The invention will be explained in more detail with reference to the associated drawings, in which.

Figure 1:
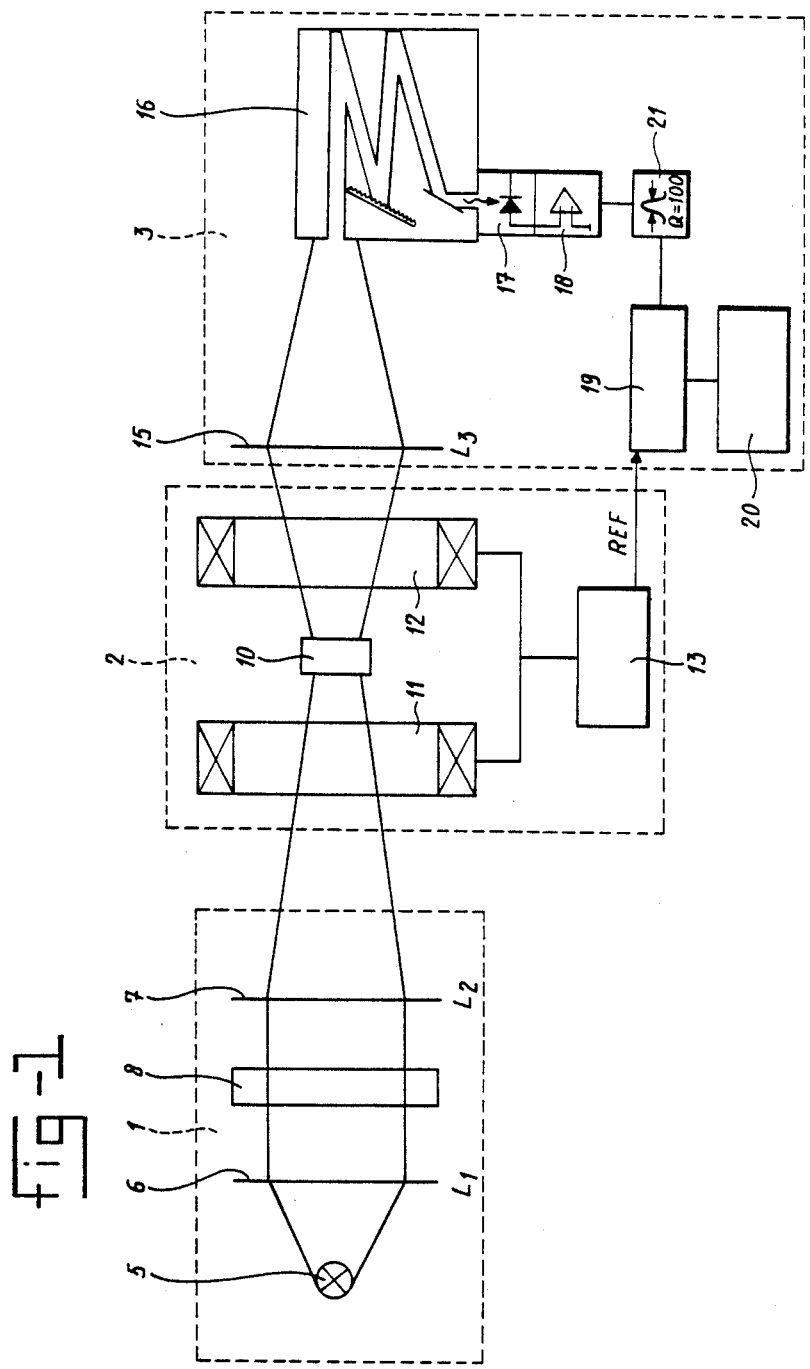
FIG. 1 shows a diagrammatic arrangement of the spectrometer according to the invention.

In FIG. 1 the spectrometer according to the invention is shown in a diagrammatic representation. Here 1, 2, and 3 respectively indicate the radiation unit, the unit for holding, cooling and/or heating of the material to be investigated, and the detection and recording unit. In the radiation unit a radiation source 5, for example a 250 W tungsten-iodine lamp, is incorporated in order to deliver a radiation beam via the lens 6, the IR filter 8, and the lens 7 to the cell 10 incorporated in the unit 2. In the said unit 2 means are also incorporated for the generation of a modulated magnetic field such as, for example, two Helmholtz coils which are fed by the supply circuit 13 with a controllable voltage, for example, at 50 Hz which can be controlled from 0 to 10 volts. By this means a current of 2A rms max. is obtained as a result of which a controllable magnetic field of up to 25 mT is produced. It is, of course, also possible to use a permanent magnetic field with an alternating amplitude modulated thereon. The modulation frequency may be varied from low to very high; a limited frequency range covers, for example, a few tens of Hz to a few kHz. Means (not shown) are also present for cooling or for heating the samples accommodated in the cell. For example, a cryostat bath can be used for delivering a stream of nitrogen gas, the temperature of the sample being monitored by means of a thermocouple embodied in the sample cell. By this means the temperature can be kept approximately constant during the investigation by adjusting the gas stream. In the unit 3 a monochromator 16 is embodied which receives the light passed through the lens 15 and delivers it to a measuring circuit at its output. This consists, for example, of a rectifier diode 17, a preamplifier 18, a selective amplifier 21, and a phase-sensitive detector (lock-in detection) 19. A reference signal originating from the supply circuit 13 is also supplied to this circuit. A recording device 20 is connected to the phase-sensitive detector 19.

In another embodiment of the spectrometer a separate excitation beam and a separate measuring beam can be used instead of a single beam in FIG. 1 intended both for excitation of the sample and for measurement of the differential absorbance. In this case the monochromator 16 can also be sited in front of the sample to be investigated in the path of the measuring beam.

Figure 2:
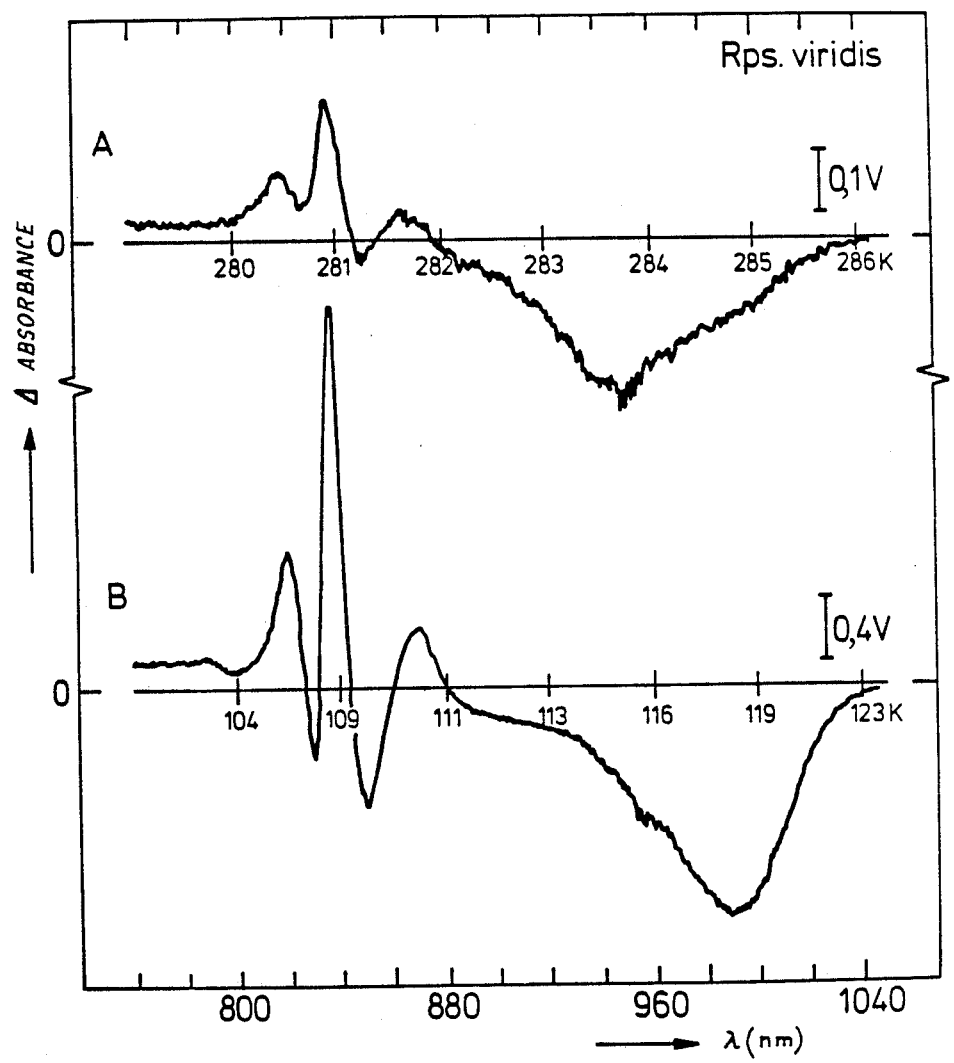
FIG. 2 shows two plots of the absorbance difference (T-S) spectrum of reaction centres in a photosynthetic bacterium at temperatures of approx. 280K. and 110K. respectively.
Figure 3:
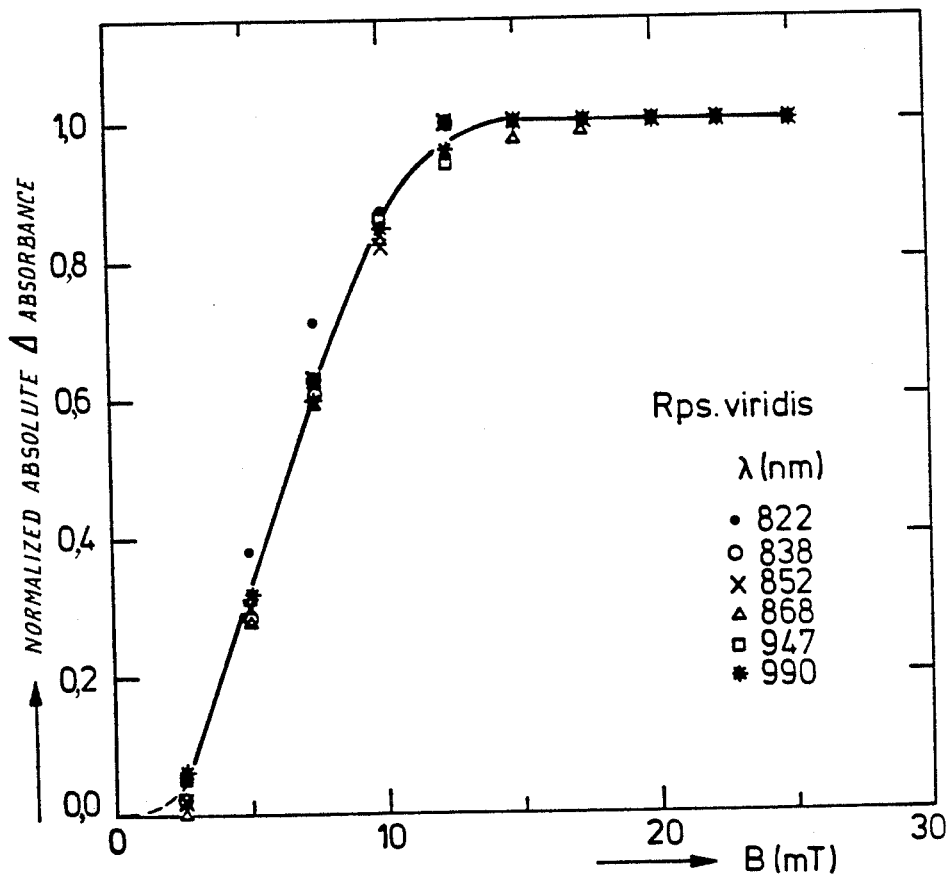
FIG. 3 shows a normalized absolute absorbance difference as a function of the magnetic field strength of reaction centres in the same bacterium as in FIG. 2.
Figure 4:
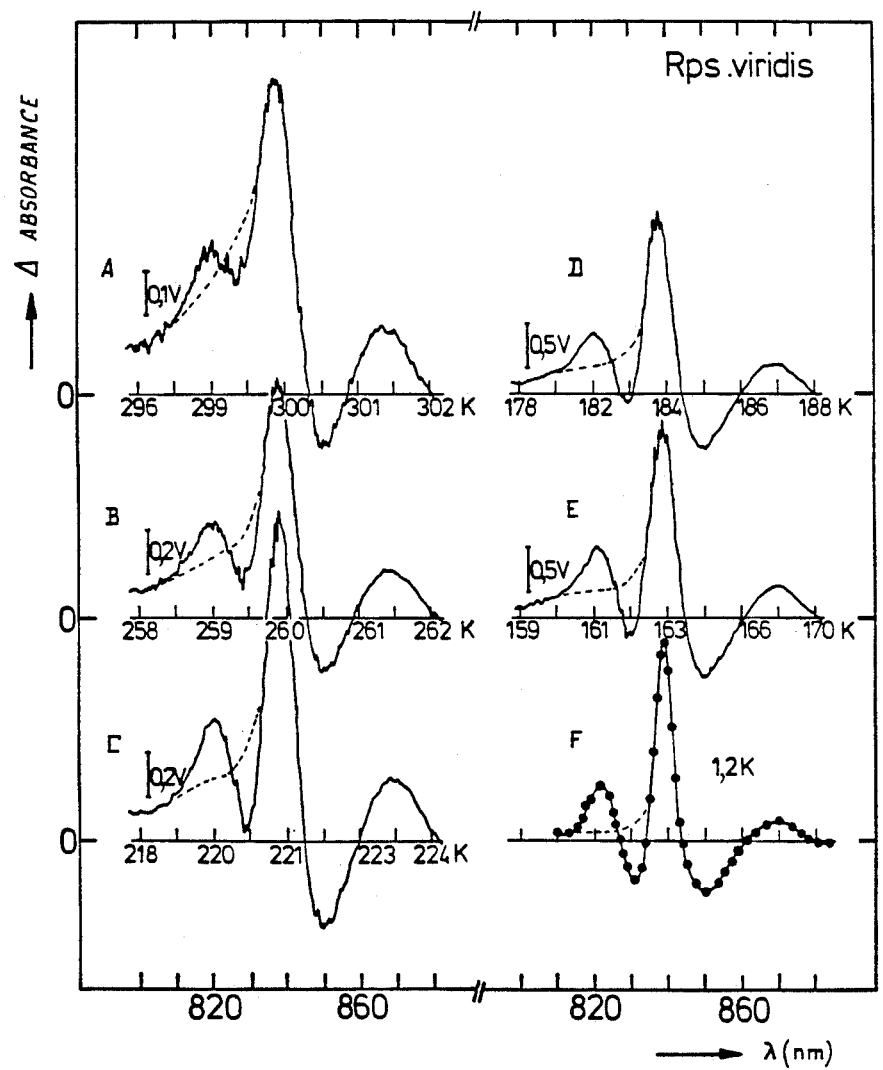
FIG. 4 shows a number of plots of the absorbance difference (T-S) spectrum of reaction centres at different temperatures in the same bacterium as in FIGS. 2 and 3.

In FIGS. 2, 3 and 4 the results are shown of the magneto-optical difference spectroscopy (MODS) measurements on an Rps. viridis bacterium. This bacterium was prepared as is described in the article mentioned in the introduction and was suspended in a 10 mM buffer solution of 4-morpholinepropanesulphonic acid (pH 8). In this process a reduction of the acceptor chain beyond $A_1$ was obtained by adding 10 mM ascorbate. For measurements below 273K. the samples were slowly frozen under illumination, care being taken that no cracks were produced. To some samples 60% v/v ethylene glycol was added before cooling.

In FIG. 2 MODS spectra of reaction centres measured at temperatures of 280K. and 110K. respectively are shown in the curves A and B. Despite the cooling by the said gas stream the sample slowly heated up during the illumination. The temperature of the sample during the wavelength scan, which lasted a few minutes, is therefore shown.

FIG. 3 shows a plot of a normalized absolute absorbance difference of the spectrum as a function of the amplitude of the 50 Hz magnetic field at a temperature of approx. 300K. Here normalization is to unity at the value of the maximum magnetic field. It is evident from this that all the bands exhibit the same magnetic field dependence, which indicates that they are all induced by the same photoinduced radical pair. In the case of this bacterium no 60% v/v ethylene glycol was added.

In FIG. 4 five MODS spectra of reaction centres in the wavelength range from 800 to 880 nm measured at temperatures of 300, 260, 220, 184 and 163K. respectively are shown in the curves A to E. For comparison, in curve F an absorbance difference spectrum is shown which has been obtained by the known absorbance detected magnetic resonance (ADMR) technique for the same bacteria at 1.2K. From the curves A to E it is evident that the trough at 828 nm exhibits a considerable change as a function of temperature from absorbance at high temperature to a sharp decrease of absorbance or bleaching at low temperature.

From the measurements reported above it is evident that the MODS technique at 280K. is comparable in sensitivity with the ADMR technique at 1.2K. This is not surprising since for bacterial reaction centres a magnetic field of 20 mT at 280K. causes a reduction in triplet yield of approximately 45%, while for the ADMR technique this is in the order of 1%. In the present method the modulation frequency of the magnetic field can, with advantage, be set high as it is only limited by the triplet decay time which is a few μs at 300K.

In the present case the MODS intensity I is proportional to the triplet yield in a zero field $\phi(o)$ and the relative magnetic field effect in the field B (mT):

$$I = \phi(o) \cdot \{[(o) - \phi(B)]/\phi(o)\} = \phi(o) [(1R)]$$

where R is approximately given by $$R = \phi(B)/\phi(o) = [3 - 2\phi(O)]^{-1}$$

The equation for R is derived on the assumption that the decay of $D^+A_1^-$ to the singlet state is much slower than the decay to the triplet state $^3D$, which condition is valid for most of the temperature range investigated. I becomes a maximum for $\phi(o)$ approx. 0.7. At room temperature $\phi(o)$ becomes approx. 0.15 and increases gradually at lower temperatures to $\phi(o)$ approx. 0.7 at 4.2K. For this reason it may be expected of the MODS sensitivity that it increases for lower temperatures, down to the temperature of liquid helium. From FIG. 2 it is evident that this expectation appears true in the measurements at least down to 110K.

Referring to FIG. 2 it is pointed out that in the spectrum of curve A the absorbance bleaching in the lower wavelength region at 960 nm exhibits a "shoulder" at 990 nm. As the temperature decreases to 110K. this shoulder increases in the curve B until the whole band exhibits a peak at 990 nm, which is the normal appearance of the absorbance bleaching occuring at long wavelengths, of reaction centres of Rps. viridis at cryogenic temperatures. These spectra indicate that the transition is gradual for the primary electron donor, and possibly reflects two states of configuration of the BChl dimeer which forms the primary donor.

In FIGS. 2 and 4 the wavelength region of the MODS spectrum between 800 and 880 nm is the most interesting. As the temperature decreases from 300 to 160K. the peaks at 822, 838, 852 and 868 nm in the curves A to E in FIG. 4 exhibit only a small variation in their relative size. The trough at 828 nm, however, becomes increasingly deeper with decreasing temperature and at 160K. even passes the zero line and at 110K. approaches the depth of the trough at 828 nm in the T-S spectrum at 1.2K. detected by ADMR shown in curve F.

In these spectra the phenomena at 822 and 828 nm and at 852 and 868 nm are clearly explained by band shifts towards the blue and red respectively of the absorbance bands of the two associated BChl pigments which adjoin the donor D. The peak at 838 nm is ascribed to a band which occurs as a consequence of one of the two BChl's which form the primary donor D when the exciton interaction between the two components of this donor D is broken by the formation of a triple state which, viewed from the point of view of time, is associated with one of the two BChl's of D.

The results obtained in this method fit into the interpretation given earlier. The change of the phenomena at 822 and 828 nm in the spectra of FIG. 4 with increasing temperature is explained by the decrease of the amplitude of the blue shift due to a broadening of the absorbance band at 828 nm along with a broadening and increasing asymmetry of the band at 838 nm (as indicated by the broken line in FIG. 4). Such a temperature-induced broadening and asymmetry of absorbance bands are normal features for photosynthetic reaction centres. From this it can be concluded that in reaction centres of Rps. viridis no charge transfer triplet state of the form $^3(D+A_o^{31})$ occurs as is assumed for Rps. sphaeroides in the publication by V. A. Shuvalov and W. W. Parson mentioned earlier. It is also pointed out that the red shift at 860 nm to some extent changes with temperature, which appears mainly to be a result of the broadening of the 838 nm band.

In the prior art it is further assumed that the associated BChl which absorbs at 830 nm is a transient electron acceptor $A_o$. From measurements by the above mentioned method it is evident that this BChl is much more sensitive to temperature-induced changes in pigment configuration than the other associated BChl which absorbs at 850 nm. Although, therefore, both associated BChl's have a virtually identical interaction with the donor D, as is evident from the comparable magnitudes in nm or the band shift of their absorbance band upon the formation of $^3D$, they are quite different in their response to changes in temperature. This asymmetry agrees with the asymmetry in their function since until now any evidence of the BChl pigment absorbing at 850 nm being involved in the electron transport has been lacking.

Experiments according to the present method have related to Rps. veridis and of necessity do not imply that a $^3(D+A_o^-)$ state does not play a role in the reaction centres of Rps. sphaeroides R-26. Preliminary MODS experiments on these reaction centres, however, give the impression that the main reason for the temperatureinduced changes in the T-S spectrum is a broadening of the absorbance bands and not the admixture of a charge transfer state.

It is pointed out that the method is not limited to the above examples, and that modifications and variants are possible within the scope of the invention. The said method is of general interest for the investigation of reactions in which processes which are dependent on magnetic fields occur and is not limited to pigment compositions. Thus, reactions during photolysis, thermolysis and electrolysis can also be investigated. The manner of detection is also not limited to absorbance but can in principle cover any optical property such as fluorescence, delayed fluorescence, phosphorescence, etc.

I claim:

1. An improved method for measuring the absorbance difference spectra of radical reactions in a material using a modulated perturbation of the concentration of reactants in radical complexes induced by radiation, the yield of substances and/or molecular states produced by recombination, and by escaping radicals being influenced, the improvement comprising the steps of:
   applying a modulated magnetic field on said material for changing the absorbance generated by the material,
   adjusting the temperature of said material over a large temperature range of approximately 160°–300° K., and
   phase-sensitively detecting/change of absorbance over said large temperature range for a wide frequency range.

2. The method as claimed in claim 1 including the step of:
   adjusting said magnetic field in the range of approximately 0–25 mT with a modulation frequency in the range of a about 20 Hz to about 10 kHz.

3. A spectrometer for carrying out the method according to claim 1 or claim 1 having a means for receiving the material to be investigated, means for heating and/or cooling the material, means for applying radiation to the material and detection means for detecting the resulting absorbance spectrum of the material being investigated, the improvement comprising:
   means for exerting a modulated magnetic field on the material being investigated,
   means of varying the temperature of the material in a wide temperature range of approximately 160°–300° K.,
   and said detector means comprises a phase-sensitive detector for converting changes in absorbance generated in said material into a dc absorbance.

* * * * *